United States Patent [19]

Strickler

[11] Patent Number: 5,264,590

[45] Date of Patent: Nov. 23, 1993

[54] PREPARATION OF TITANIUM (III) COORDINATION COMPLEXES

[75] Inventor: Jamie R. Strickler, Baton Rouge, La.

[73] Assignee: Ethyl Corporation, Richmond, Va.

[21] Appl. No.: 41,098

[22] Filed: Apr. 1, 1993

[51] Int. Cl.⁵ .................. C07D 493/12; C07F 7/28
[52] U.S. Cl. ................... 549/208; 549/210; 556/54; 556/56
[58] Field of Search .............. 556/54, 56; 549/208, 549/210

[56] References Cited

U.S. PATENT DOCUMENTS 3,769,233 10/1973 Hermans et al. .............. 252/429 A
4,210,736 7/1980 Baekelmans et al. .............. 526/142

FOREIGN PATENT DOCUMENTS 601769 9/1990 Australia .
0334411 9/1989 European Pat. Off. .
2320309 3/1977 France .

OTHER PUBLICATIONS

Fowles et al., J. Chem. Soc., pp. 5873-5878 (1963).
Clark et al., J. Chem. Soc., pp. 379-387 (1963).

*Primary Examiner*—José G. Dees
*Assistant Examiner*—Profirio Nazario-Gonzalez
*Attorney, Agent, or Firm*—David N. Bunnell

[57] ABSTRACT

Ti(III) coordination complexes with ethers are prepared by the steps of (a) forming an ether complex of a Ti(IV) salt by adding a stoichiometric excess of an ether to said salt, and then (b) reducing said complex with an organometallic reducing agent such as an aluminum alkyl or a lithium compound to form a Ti(III)-ether coordination complex.

12 Claims, No Drawings

PREPARATION OF TITANIUM (III) COORDINATION COMPLEXES

The invention relates generally to the preparation of Ti(III) coordination complexes and specifically to the preparation of Ti(III) coordination complexes by the reduction of Ti(IV) salts using an organometallic or metal hydride reducing agent.

Ti(III) coordination complexes with ethers are useful intermediates in the formation of Ti(III) metallocene compounds such as dicyclopentadienyl titanium chloride. The metallocene compounds, usually in combination with activators such as an for stereospecific olefin polymerization.

The Ti(III) coordination complexes can be produced from the hydrogen reduced form of a salt such as $TiCl_3$, but this is expensive. A process has now been developed which provides a one-pot synthesis of Ti(III) coordination complexes starting with inexpensive Ti(IV) salts.

In accordance with this invention there is provided a process for preparing a Ti(III) coordination complex by the reduction of a Ti(IV) salt, said process comprising the steps of (a) forming an ether complex of said Ti(IV) salt by adding a stoichiometric excess of an ether to said salt, and then (b) reducing said complex with an organometallic or a metal hydride reducing agent to form a Ti(III)-ether coordination complex.

The anions of the Ti(IV) salts for use as starting materials are not critical and usually have the formula $TiX_4$ where X is halogen. The preferred Ti(IV) compound is $TiCl_4$.

Non-limiting examples of ethers for use in forming the coordination complexes include ethylene glycol dimethyl ether (DME), diglyme, triglyme, tetraglyme, tetrahydrofuran, and the like.

Suitable organometallic and hydride reducing agents include aluminum alkyls and lithium compounds, such as lithium alkyls or a lithium hydride. The aluminum alkyls preferably contain two or three alkyl groups each having from 1 to about 20 carbon atoms. Non-limiting examples of aluminum alkyls include triethylaluminum, tri-n-propylaluminum, tri-n-butylaluminum, and diisobutylaluminum hydride, and the like.

Non-limiting examples of specific lithium compounds include ethyl lithium, n-butyl lithium, sec-butyl lithium, n-propyl lithium, lithium aluminum hydride, and the like.

An inert hydrocarbon solvent can be used when forming the ether complexes of Ti(IV) salts. For example, pentane, isopentane, hexane, cyclohexane, heptane, octane, toluene and the like. The amount of solvent can range from about 20 to 70 percent by volume of the total volume of reaction mixture. Preferably, the ether is added in a large excess of 10 to 50 equivalents per equivalent of Ti(IV) salt, so as to form a slurry of Ti-(IV)-ether complex in an ether and hydrocarbon solvent mixture. The reducing agent is then added in about an equivalent amount to the complex (from about 0.8 to 1.1 equivalent of reducing agent per equivalent of complex). The reaction is very slow at room temperature. Heating the mixture to temperatures of from about 50 to 80° C produces good yields (85-98%) of product in about 1 to 4 hours.

The invention is further illustrated by, but is not intended to be limited to, the following examples.

EXAMPLE 1

Synthesis of $TiCl_3(THF)_3$ $TiCl_4$ (10.10 g, 53.2 mmol) and 50 mL of dry, distilled heptane were placed in a 500 mL round-bottomed flask in a drybox. This clear solution was stirred and then 150 mL of dry, distilled THF were added dropwise. Approximately 5 mL were first added over 5 minutes. This reaction was exothermic and a yellow crystalline solid of $TiCl_4(THF)_2$ formed. The solution became quite thick. The rate of addition was then increased so that the remaining THF was added in just a couple of minutes. A more easily stirred slurry resulted. Neat triisobutylaluminum (TIBA, 10.40 g, 52.4 mmol) was then added to the slurry dropwise over 5-10 minutes. After all the TIBA was added, a greenish-yellow slurry was present. The slurry was then taken out of the drybox and heated to 50°-65° C. for 3.5 hours under a slow flow of nitrogen vented through an oil bubbler. The slurry turned blue. The reaction was allowed to cool to ambient temperature and then the solids were isolated by filtration on a coarse 150 mL frit. The solids were washed with two portions of heptane and dried in vacuo. The yield of blue, crystalline solids of $TiCl_3(THF)$ was 18.15 g (49.0 mmol) or 92 %. The solids were analyzed by ICP and wet chemical analysis (see Table I below).

EXAMPLE 2

Synthesis of $TiCl_3(DME)_{1.5}$ $TiCl_4$ (5.05 g, 26.6 mmol) and 70 mL of dry, distilled heptane were placed in a 250 mL schlenk flask in the drybox. Anhydrous ethylene glycol dimethyl ether (DME) was then added to this clear solution dropwise. The DME was added slowly at first as this reaction is exothermic. A yellow crystalline solid of $TiCl_4(DME)$ precipitated. The rate of addition was then increased after a few milliliters were added. After 75 ml of DME were added, neat triisobutylaluminum (TIBA, 5.19 g, 26.2 mmol) was added to the slurry dropwise in approximately one minute. The solution darkened and a green solid formed. The slurry was then taken out of the drybox and heated to 65°-70° C. for 3 hours under a flow of nitrogen vented through an oil bubbler. The slurry turned blue after one hour. The reaction was allowed to cool to ambient temperature and then the solids were isolated by filtration on a coarse 60 mL frit. The solids were washed with two portions of heptane and dried in vacuo. The yield of fine blue solids of $TiCl_3(DME)_{1.5}$ was 7.51 g (25.9 mmol) or 97.5%. The solids were analyzed by ICP and wet chemical analysis (see Table I below).

TABLE I

|  | $TiCl_3(THF)_3$ | | $TiCl_3(DME)_{1.5}$ | |
|---|---|---|---|---|
|  | Theoretical | Found | Theoretical | Found |
| Ti, % | 12.93 | 13.1 | 16.55 | 16.8 |
| Al, ppm | 0 | 26 | 0 | 99.5 |
| Cl, % | 28.70 | 28.6 | 36.74 | 36.4 |
| i-Bu, % | 0 | 0.0 | 0 | 0.0 |

EXAMPLE 3

Synthesis of $TiCl_3(THF)_3$ at Ambient Temperature

In a 100 mL flask were placed $TiCl_4$ (2.06 g, 10.9 mmol) and approximately 12 mL of hexanes. This solution was stirred with a magnetic stirrer and 25 mL of THF were added dropwise. Yellow solids formed. Triisobutylaluminum (2.09 g, 10.5 mmol) was then added dropwise over several minutes. The yellow slurry slowly took on a green color. After 6 hours, the solids were blue and the mother liquor was green. After stirring overnight (22 hours), the blue solids were filtered on a coarse frit, washed with 20 mL of THF and dried in vacuo. The yield of blue solids was 3.43 g (85 %).

What is claimed is:

1. A process for preparing a Ti(III) coordination complex by the reduction of a Ti(IV) salt, said process comprising the steps of (a) forming an ether complex of said Ti(IV) salt by adding a stoichiometric excess of an ether to said salt, and then (b) reducing said complex with an organometallic or metal hydride reducing agent to form a Ti(III)-ether coordination complex.

2. The process of claim 1 wherein said ether is added in an amount to provide 10 to 50 equivalents of ether per equivalent of Ti(IV) salt.

3. The process of claim 2 wherein said ether is selected from the group consisting of tetrahydrofuran, ethylene glycol dimethyl ether, diglyme, triglyme, and tetraglyme.

4. The process of claim 3 wherein said reducing agent is selected from a lithium compound and an aluminum alkyl and said reducing agent is added in about an equivalent amount to said Ti(IV) salt.

5. The process of claim 1 wherein step (b) is at a temperature of from about 20° to 80° C.

6. The process of claim 1 wherein step (b) is at a temperature of from about 50° to 80° C.

7. The process of claim 4 wherein said reducing agent is an aluminum alkyl which contains alkyl groups having from 1 to about 20 carbon atoms.

8. The process of claim 7 wherein said aluminum alkyl is selected from triethylaluminum, tri-n-butylaluminum, triisobutylaluminum, tri-n-propylaluminum, tri-n-hexylaluminum, tri-n-octylaluminum and diisobutylaluminum hydride.

9. The process of claim 1 wherein said Ti(IV) salt has the formula $TiX_4$ wherein X is halogen.

10. The process of claim 9 wherein said Ti(IV) salt is $TiCl_4$ and said ether is THF such that the product Ti(III)-ether coordination complex is $TiCl_3(THF)_3$.

11. The process of claim 9 wherein said Ti(IV) salt is $TiCl_4$ and said ether is DME such that the product Ti(III)-ether coordination complex is $TiCl_3(DME)_{1.5}$.

12. The process of claim 4 wherein said reducing agent is a lithium alkyl or a lithium hydride.

* * * * *